United States Patent [19]

Albrektsson et al.

[11] Patent Number: 5,741,262
[45] Date of Patent: Apr. 21, 1998

[54] HIP JOINT PROSTHESIS

[75] Inventors: Bjorn Albrektsson; Magnus Jacobsson, both of Gothenburg; Lars Carlsson; Tord Rostlund, both of Kullavik; Stig Wennberg, Angered, all of Sweden

[73] Assignee: Astra Aktiebolag, Sodertalje, Sweden

[21] Appl. No.: 473,564

[22] Filed: Jun. 6, 1995

Related U.S. Application Data

[62] Division of Ser. No. 290,915, Aug. 22, 1994.

[30] Foreign Application Priority Data

Feb. 28, 1992 [SE] Sweden .................. 9200597

[51] Int. Cl.⁶ .................................. A61B 17/56
[52] U.S. Cl. .................................. 606/80; 623/23
[58] Field of Search ................... 606/89, 86, 96, 606/80, 79; 623/18, 22, 23

[56] References Cited

U.S. PATENT DOCUMENTS

| | | |
|---|---|---|
| 2,682,265 | 6/1954 | Collison . |
| 2,685,877 | 8/1954 | Doselle . |
| 2,785,673 | 3/1957 | Anderson ............................ 606/96 |
| 3,002,514 | 10/1961 | Deyerle ............................ 606/96 |
| 4,005,495 | 2/1977 | Locke et al. . |
| 4,795,473 | 1/1989 | Grimes . |
| 4,976,740 | 12/1990 | Kleiner . |
| 5,342,363 | 8/1994 | Richelsoph ............................ 606/79 |
| 5,376,125 | 12/1994 | Winkler . |
| 5,429,641 | 7/1995 | Gotfried ............................ 606/67 |

FOREIGN PATENT DOCUMENTS

| | | |
|---|---|---|
| 2438470 | 5/1980 | France . |
| 2674122 | 9/1992 | France . |
| 2724234 C2 | 12/1977 | Germany . |
| 2854334 B2 | 6/1980 | Germany . |
| 3420035 A1 | 5/1984 | Germany . |
| WO 91/07932 | 6/1991 | WIPO . |

*Primary Examiner*—Guy V. Tucker
*Attorney, Agent, or Firm*—White & Case

[57] ABSTRACT

The invention relates to a hip joint prosthesis comprising an attachment part for a ball unit (18) being designed to be anchored in the neck of a human femur (collum femoris), said attachment part, which is intended to be inserted into a channel (5, 14) extending through the femoral collum, being provided with parts for carrying a ball or caput (18) intended to be attached to the collum after removal of the head of the collum. The attachment part also comprises a fixture part comprising two main parts, a first part (1) which is to extend through a bore-hole (5) from the collum femoris towards the outer side of the femur and a second part (2) intended to fit into a cylindrical cavity cut into the cancellous bone of the collum.

8 Claims, 3 Drawing Sheets

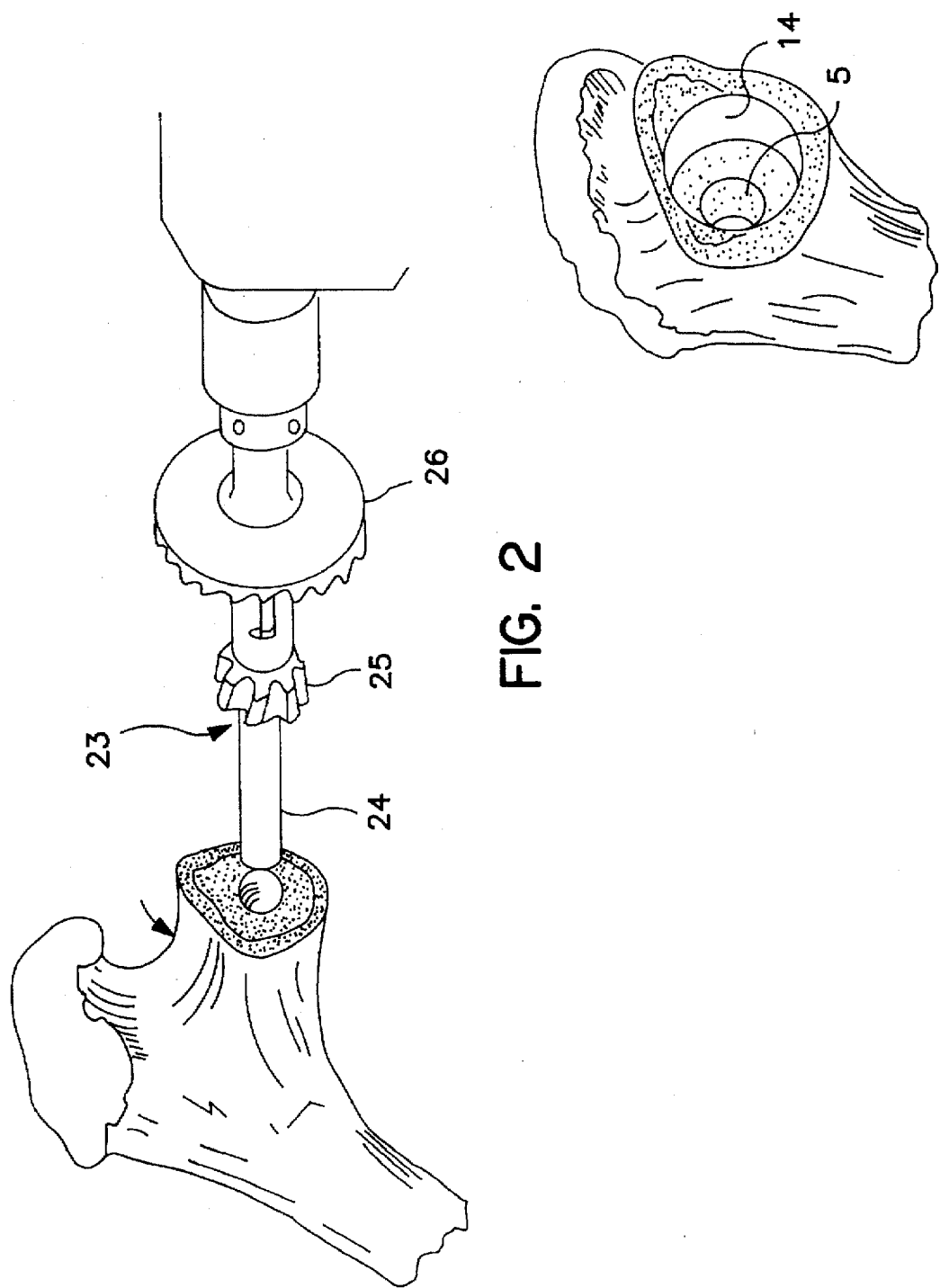

HIP JOINT PROSTHESIS

This application is a divisional of application Ser. No. 08/290,915, filed Aug. 22, 1994, still pending, which is a U.S. national stage application of International application No. PCT/SE93/00169, filed Feb. 26, 1993.

TECHNICAL FIELD OF THE INVENTION

The invention relates to a hip joint prosthesis for permanent anchoring in the human hip joint comprising an attachment part for a ball unit designed to be anchored in the neck of a human femur (collum femoris), said attachment part, which is intended to be inserted into a channel extending through the femoral collum, being provided with parts for carrying a ball or caput intended to be attached to the collum after removal of the head of the femur.

BACKGROUND OF THE INVENTION

The present invention is a development of a hip joint prosthesis of the kind disclosed in WO 89/11837. This document inter alia discloses a hip joint prosthesis comprising a primary fixture in the shape of a sleeve, said sleeve being intended to be inserted into a central hole bored longitudinally through the collum femoris from the outer side of the femur and a secondary fixture in the shape of a cap having a spherical shape intended to be attached to and cover the end of the collum femoris when the head of the collum has been removed partly or entirely and the outside of remaining end has been cut to a cylindrical shape. The primary and the secondary fixtures are interconnected by means of a bolt which at one end has an internal thread. The bolt is to be inserted into the sleeve and its internal thread is to be made to engage a central, threaded stud projecting from the spherical cap. When the bolt is tightened, the cap is pressed over the cylindrically cut caput or end of the collum.

The prior art device thus is relatively complicated, both in construction and use.

In some applications it may furthermore not be suitable to use this prior art device. One reason for this is that the shape of the collum may make it difficult to retain enough cortical bone to give the secondary fixture or cap a firm support, since the shape of the collum may vary to a great extent.

This prior art device is also designed to be inserted in a two-seance procedure, i.e. some parts of the prosthesis are to be inserted in a first operation, the remaining parts being inserted later in a second operation after a healing period of a few months.

Other similar prior art is disclosed for instance in DE-A1-28 45 231, DE-A1-27 24 040, U.S. Pat. No. 4,795,473 and U.S. Pat. No. 4,005,495.

The object of the invention is to achieve a hip joint prosthesis which is simple in construction and use and which is particularly suited for insertion in a one-seance operation and which can be adapted to fit different conditions.

BRIEF DESCRIPTION OF THE INVENTIVE CONCEPT

According to the invention the attachment part in a hip joint prosthesis of the kind described above also comprises a fixture part comprising two main parts, a first part which is to extend through a bore-hole from the collum femoris towards the outer side of the femur and a second part intended to fit into a cylindrical cavity cut into the cancellous bone of the collum.

The fixture can be made in one piece but, in one preferred embodiment, comprises two separate parts which are firmly attached to each other before the fitting of the fixture into the femur.

This will result in that the cortical bone will remain intact to a larger degree and that the load conditions will be such that a physiologically appropriate load on the upper part of the collum can be achieved. Forces can be transferred from the fixture to the femur without any noticable movements by means of the direct or indirect contact with the inside of the cortical bone in the collum.

BRIEF DESCRIPTION OF THE APPENDED DRAWINGS

FIG. 1 is a section of a femur with the fixture mounted, the femur but not the fixture being sectioned, FIG. 2 illustrates a confined reamer and cutter for shaping the recess in the collum for the fixture, FIG. 3 illustrates the shape of the recess in the collum, and FIGS. 4 and 5 show a section of the collum with the recess with and without the fixture.

DETAILED DESCRIPTION OF THE PREFERRED EMBODIMENT OF THE INVENTION

Figure 1:
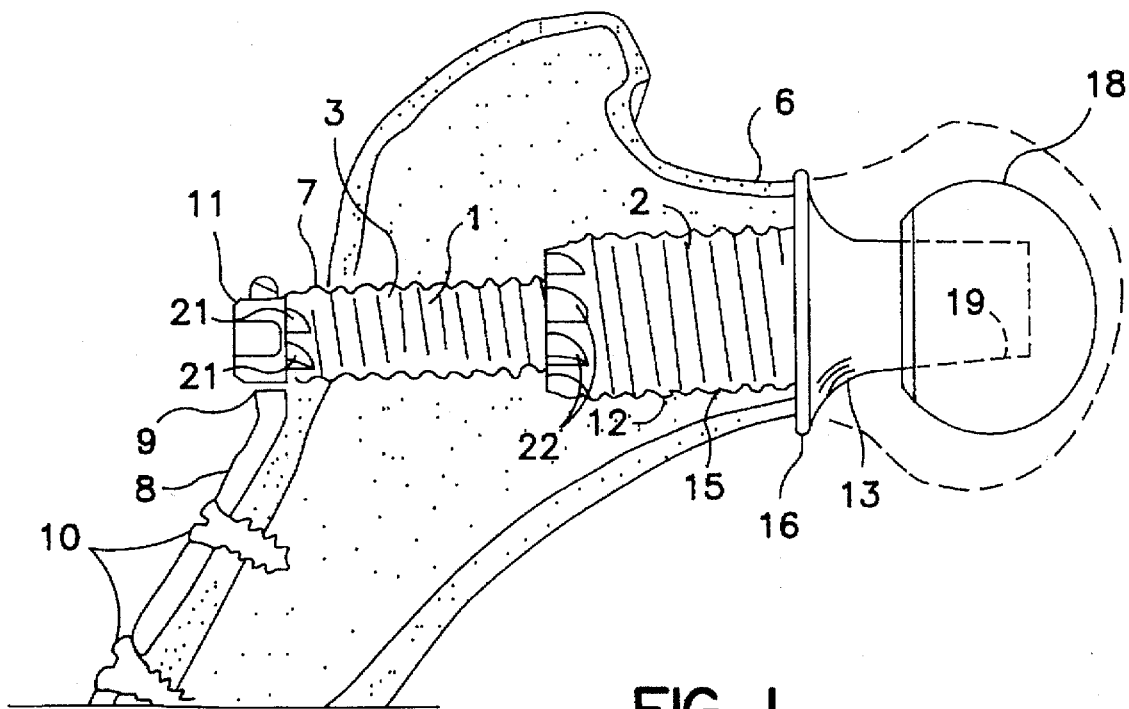
Figures 4, 5:
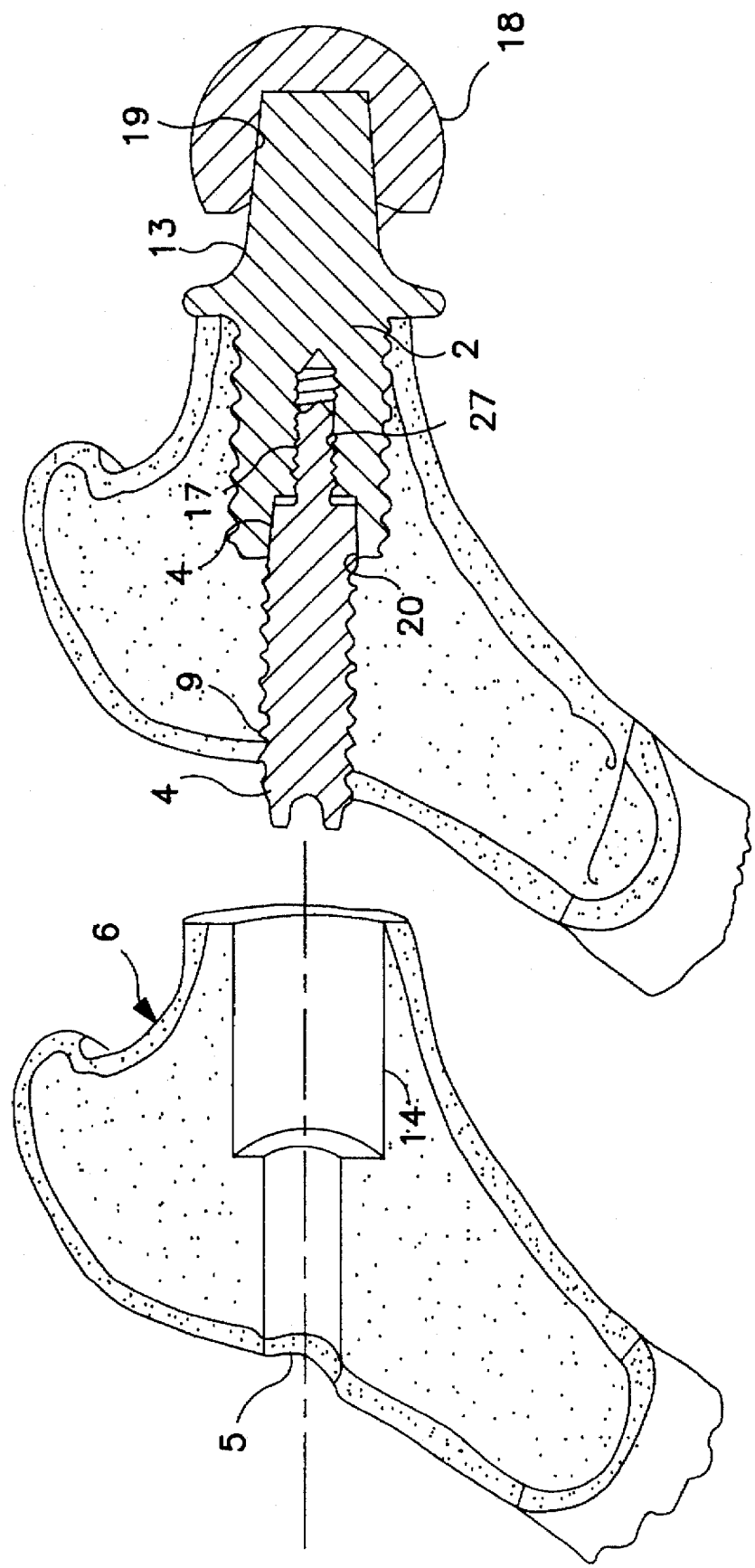

As can be seen in FIGS. 1 and 5, the fixture comprises two main parts, an elongate, cylindrical first part 1 and a second plug-like, generally cylindrical part 2. The first part 1 is provided with relatively large and widely spaced threads 3 on a major or main part of its outside, the remainder 4 of its outside being smooth and slightly conical. On the end surface of the slightly conical end of the first part 1 a narrow, threaded part 17 is located which is coaxial with the first part 1.

The first part 1 is to fit in a channel or hole 5 drilled longitudinally and centrally through the collum 6. The head 7 of the first part 1 is to be located on the outside of the femur and may, but need not (of FIG. 5), be locked against rotation by means of an elongate plate 8 having a recess 9 with a shape complementary to the shape of the head 7 of the first part 1. The elongate plate is attached to the femoral shaft by means of screws 10. The head 7 of the first part may, but again need not, also be covered by means of a nut 11 having threads being complementary to the threads 3.

A longitudinal bore being provided with threads is provided in the end surface or head 7 of the first part 1. This bore is complementary to a threaded tap on a guide rod having the same diameter as the first part.

The second part 2 is in the shape of a cylindrical plug. One part 12 of the plug is to be inserted into a recess 14 cut in the collum, cylindrically and co-axially with the channel or hole 5. The outside of the part 12 of the plug is provided with threads 15 similar to the threads 3 on the first part 1. The plug 12 is delimited by a circumferential flange 16 limiting the insertion of the plug 12 into the cavity or recess 14. The plug 12 further is provided with a central hole 26 having two parts, an inner, threaded part 27 having an inner diameter corresponding to the outer diameter of the threaded narrow part 17 of the first part 1 and an outer, unthreaded part 20 which is slightly conically flaring in a way corresponding to the unthreaded part 4 of the first part 1 of the fixture.

The threaded parts 17, 27 as well as the threaded parts 1, 12 may be right-handed or left-handed depending on which side of the body they are to be mounted.

The threads on the first and second parts preferably are self-tapping. This can for instance be achieved in that the distal ends of the first and the second part are provided with sharpedged recesses 21, 22 in a manner similar to self-tapping screws. The recesses 22 on the second part 2 extend all the way to the end surface of the second part. The recesses 21 on the first part 21 do however not extend all the way to the end surface or head 7, since this part of the first part 1 normally is to be located in the soft tissue and for this reason should not have any sharp edges. This is especially important if no covering nut 11 is used.

The first part 1 is made in several versions with different lengths and the second part 2 is made in several versions with different diameters of the plug part 12.

The plug finally is provided with a conical projection or attachment cone 13 for carrying the ball or caput 18 which is provided with a complementary conical hole 19.

The first and the second part of the fixture preferably are made of c.p. (commercially pure) titanium and may be subjected to a suitable surface treatment. The elongate plate 8 preferably is made of a suitable titanium alloy, whereas its attachment screws 10 preferably should be made of c.p. titanium and for instance have a diameter of 4.5 mm. The attachment cone can be made of a titanium alloy or of c.p. titanium and should be treated in a suitable way to minimize the risk for fretting corrosion. The caput preferably should be made of a ceramic material, also in order to minimize the risk for fretting corrosion.

The socket or acetabulum is not part of the present invention and may be of any commerciably available kind which is suitable.

The operation for implanting the hip joint prosthesis is preferably performed in a one-stage operation.

Any differences in the length of the legs are measured. An estimate of the narrowest diameter of the collum is made in order to obtain an idea of the size of the implant to be used.

With great care not to disturb the blood circulation, the hip is exposed through an anteriolateral approach. The hip joint is then dislocated. A guide instrument for a cutting tool is attached. The caput is then cut off and removed.

The narrowest part of the collum is measured directly in order to obtain further information regarding the size of the implant.

A drill is then oriented by means of the guide instrument in such a way relative to the surface of the section that the drill is aligned with the longitudinal extent of the collum and is located at the center of a circle which touches the inside of the cortical bone in the section in at least three points. The diameter of this circle is determined. A hole 5 having a diameter corresponding to the diameter of the first part 1 is then drilled through the collum from the surface of the section, cf FIG. 2.

The cylindrical recess or hole 14 is then cut longitudinally in the collum from the direction of the caput by means of a rotary cutting (milling) tool 23. The cutting tool is provided in several sizes, each size corresponding to one size of a second part.

The cutting tool comprises a cylindrical, elongate guide part 24 which has a diameter corresponding to the diameter of the hole 5. The tool further comprises a reamer 25 which is coaxial with the guide part 24, the diameter thereof being chosen to correspond to the diameter of the above circle touching the cortical bone. The diameter and the length of the reamer also corresponds to one of several standard sizes of the second part 2. The tool 23 finally also comprises a surface cutter 26.

The guide 24 is inserted into the hole 5 until the reamer 25 engages the surface of the section. The cylindrical recess 14 is then cut by means of the reamer until the surface cutter 26 engages and machines the surface of the section. The object of this machining is to ensure that the surface of the section is smooth and is oriented orthogonally relative to the longitudinal axis of the hole 5. This is important since the longitudinal direction of the collum not necessarily is orthogonal relative to the surface of the section. The resulting cavity 5, 14 can be seen in FIG. 3.

A first part having a suitable length and a second part having a suitable diameter are then chosen and attached to each other by means of the threaded part 17 on the first part 1 and the threaded hole 27 in the second part. The respective conically shaped parts 4, 20 on the first and the second part will ensure a secure and tight connection between the two parts.

The above-mentioned guide rod or extension, which has a diameter corresponding to the diameter of the hole 5, is then mounted on the free end of the first part 1 by means of the threaded bore therein. The guide rod is then inserted into the hole 5 until the threads on the first or the second part engage the bone tissue in the collum. The fixture is then screwed into the hole 5 and the recess 14 whilst being kept aligned by said guide, threads simultaneously being cut into the bone tissue on the inside of the hole 5 and the recess 14 in the collum until the flange or collar 16 abuts the cortical bone on the cut end surface of the collum. Due to the machining by means of the cutter 26, the flange or collar 16 will fit snugly against the surface of the section. The guide rod is then removed.

Finally a ball or caput 18 is mounted on the attachment cone 13 and a reduction or repositioning of the joint is made in order to test the stability of the joint and the length of the leg. The length of the leg is corrected by using caputs having differently sized conical holes 19. The operation is then completed.

After the operation the hip joint soon can be subjected to loads to a limited extent since the design of the fixture will ensure that the fixture is stable to an extent which is sufficient to allow osseointegration.

Possible modifications of the invention

The invention of course can be varied in many ways within the scope of the appended claims.

As mentioned above, the fixture can be made in one, integral part, which may be advantageous in some applications even if it might greatly increase the number of different types to be kept in stock.

It is also possible to allow the first part of the fixture to end in the cancellous bone tissue before it reaches the cortical bone tissue on the outside of the femur, which may eliminate the necessity of disturbing the cortical bone and the soft tissue on the outer side of the femur.

It may not always be necessary to achieve the three-point contact between fixture and cortical bone in the collum femoris discussed above. This may be of particular importance if the collumfemoris has such a shape that it more or less is impossible to obtain said three-point contact. In some cases it may also be more important to center or orient and size the fixture in such a way that a maximal bone contact is obtained. In one extreme it might also be conceivable to design or choose the first and second part of the fixture to have the same diameter. However, if the lateral femoral cortex is to be penetrated, the diameter of the first part should be kept at a minimum.

To express the advantages of the device somewhat differently, the hip joint prosthesis as set forth in the appended claims provides a cylindrical, longitudinal fixture which may be centered in the collum femoris. This allows a dimensioning of the device permitting a maximal bone contact whilst minimizing the risk of perforating the cortical bone in the collum femoris. The fixture permits the penetration of the lateral femoral cortex by means of a threaded extension thereof which may have a smaller diameter than the rest of the fixture. The fixture may have a flange or abutment collar which may be made to fit exactly against the cut end of the collum femoris by means of a guided bone cutting tool. The fixture can be positioned by means of a drill guide permitting the above centering in conjunction with a centering guide. This, in conjunction with a self-tapping design of the fixture, preferably in pure or almost pure titanium, allows the achievement of an optimal bone contact.

We claim:

1. A method for permanent anchoring of a fixture for a hip joint prosthesis in the neck of a human femur comprising the steps of:

resecting the head of the femur to expose a section of the femur neck, drilling into the femur neck through the exposed femur neck section in a predetermined forward direction towards a position below the greater trochanter to form a cylindrical bore in the femur neck which extends in the predetermined forward direction and which is stepped into a rearward portion of a first diameter having an open end in the exposed femur neck section and a coaxial forward portion of a second diameter less than the first diameter extending forwardly from the rearward portion, providing a fixture having a cylindrical anchoring portion of stepped screw threaded outer surface profile and diameters corresponding essentially to those of the bore, and anchoring the fixture in the femur neck by inserting the cylindrical anchoring portion of the fixture into the bore by translation of the fixture in the predetermined forward direction.

2. A method according to claim 1, wherein the first diameter of the rearward portion of the bore is so selected that cortical bone from the outer peripheral layer of cortical bone in the femur is presented in the boundary wall of the rearward portion of the bore for screw threads on the outer surface of the cylindrical anchoring portion of the fixture to register in.

3. A method according to claim 2, wherein the first diameter of the rearward portion of the bore is so selected that the circumference of the rearward portion of the bore contacts the outer peripheral layer of cortical bone in the femur in at least three circumferentially spaced locations.

4. A method according to claim 1, wherein the bore is formed by drilling a first bore having the second diameter in the predetermined forward direction through the exposed femur neck section into the femur neck towards a position below the greater trochanter and then drilling a second bore having the first diameter in the predetermined forward direction through the exposed femur neck section coaxially with the first bore to a position between the exposed femur neck section and the forward end of the first bore.

5. A method according to claim 4, wherein the second bore is formed by providing a drill having a cylindrical forward guide section of essentially the second diameter and a coaxial rearward drill section for drilling the second bore, inserting the guide section of the drill into the open end of the first bore in the exposed femur neck section and translating the drill in the predetermined forward direction under the guiding action of the guide section until the drill section of the drill reaches the position between the exposed femur neck section and the forward end of the first bore.

6. A method according to claim 5, wherein the rearward drill section includes grinding means which on translation of the drill in the predetermined forward direction grinds the exposed femur neck section to a plane which is orthogonal to the predetermined forward direction.

7. A method according to claim 1, wherein the bore is formed so as to extend in the predetermined forward direction between the open end in the exposed femur neck section and an open end in the femur outer surface positioned below the greater trochanter.

8. A method according to claim 1, wherein the screw threads on the outer surface of the cylindrical anchoring portion of the fixture are self-tapping.

* * * * *